United States Patent [19]

Smith, Jr. et al.

[11] Patent Number: 5,248,837
[45] Date of Patent: Sep. 28, 1993

[54] METHOD FOR CONTROLLING CATALYTIC DISTILLATION ETHERIFICATIONS

[75] Inventors: Lawrenc A. Smith, Jr.; Edward M. Jones, Jr.; Henry J. Semerak, all of Pasadena, Tex.

[73] Assignee: Chemical Research & Licensing Company, Pasadena, Tex.

[21] Appl. No.: 964,496

[22] Filed: Oct. 21, 1992

[51] Int. Cl.$^5$ ............................................. C07C 41/06
[52] U.S. Cl. ..................................................... 568/697
[58] Field of Search ........................................ 568/697

[56] References Cited

U.S. PATENT DOCUMENTS

| | | | |
|---|---|---|---|
| 4,232,177 | 11/1980 | Smith, Jr. | 585/324 |
| 4,307,254 | 12/1981 | Smith, Jr. | 568/697 |
| 4,336,407 | 6/1982 | Smith, Jr. | 568/697 |
| 4,504,687 | 3/1985 | Jones, Jr. | 568/697 |
| 4,978,807 | 12/1990 | Smith, Jr. | 568/697 |
| 5,118,873 | 6/1992 | Smith, Jr. | 568/697 |

Primary Examiner—Howard T. Mars
Attorney, Agent, or Firm—Kenneth H. Johnson

[57] ABSTRACT

A process for the etherification of isoolefins with alcohols is provided wherein the reaction occurs simultaneously with separation of the ether product and reactants. To assure proper alcohol concentration throughout the reaction zone, the alcohol concentration is measured at a point below the catalyst bed and controlled to that which maximizes ether production while preventing alcohol from leaving the reactor with ether product.

6 Claims, 3 Drawing Sheets

METHOD FOR CONTROLLING CATALYTIC DISTILLATION ETHERIFICATIONS

BACKGROUND OF THE INVENTION

1. Field of the Invention

The present invention relates to the etherification of isoolefins, particularly C4 and C5 isoolefins, with a alcohol such as methanol, to produce the corresponding tertiary ether. More particularly the invention relates to a process wherein a catalytic distillation process is used in the process and wherein the concentration of the alcohol below the catalyst bed is controlled to prevent the concentration of the alcohol from becoming too low (and thus reducing the conversion) or too high (and thus contaminating the ether product).

2. Related Information

The reaction of an alcohol and an olefin and concurrent separation of the reactants from the reaction products by fractional distillation has been practiced for some time. The process is variously described in U.S. Pat. Nos. 4,232,177; 4,307,254; 4,336,407; 4,504,687; 4,987,807; and 5,118,873 all commonly assigned herewith.

Briefly the alcohol and isoolefin are fed to a distillation column reactor having a distillation reaction zone containing a suitable catalyst, such as an acid cation exchange resin, in the form of catalytic distillation structure, and also having a distillation zone containing inert distillation structure. As embodied in the etherification of $iC_4=$'s and/or $iC_5=$'s the olefin and an excess of methanol are first fed to a fixed bed reactor wherein most of the olefin is reacted to form the corresponding ether, methyl tertiary butyl ether (MTBE) or tertiary amyl methyl ether (TAME). The fixed bed reactor is operated at a given pressure such that the reaction mixture is at the boiling point, thereby removing the exothermic heat of reaction by vaporization of the mixture. The fixed bed reactor and process are described more completely in U.S. Pat. No. 4,950,803 which is hereby incorporated by reference.

The effluent from the fixed bed reactor is then fed to the distillation column reactor wherein the remainder of the $iC_4=$'s or $iC_5=$'s are converted to the ether and the methanol is separated from the ether which is withdrawn as bottoms. The $C_4$ or $C_5$ olefin stream generally contains only about 10 to 60 per cent olefin, the remainder being inerts which are removed in the overheads from the distillation column reactor.

As noted above in the etherification of olefins with an alcohol there is preferably an excess of the alcohol available in the reactor. This means that there is an excess of methanol in the reaction distillation zone of the distillation column reactor. In the distillation column reactor the methanol forms a minimum boiling azeotrope with either of the olefins. In the case of $C_4$'s the azeotrope is only slightly more volatile than the $C_4$'s, and therefore the methanol tends to remain in a relatively constant concentration with the $C_4$'s throughout the column. Because the concentration of the methanol in the $C_4$ azeotrope is only about 4% (depending upon the composition of the $C_4$ mixture), it is necessary to operate with a methanol concentration somewhat below 4% to avoid exceeding the azeotrope, in which case the excess will first accumulate in the column and then leave with the MTBE bottoms.

In the case of the $C_5$'s, the azeotrope contains about 12 wt % methanol, and the boiling point of the azeotrope is 10 to 15 degrees F. below that of the corresponding $C_5$'s. Thus, if the net flow of methanol into the column (allowing for that reacting in the column) is less than the azeotrope concentration in the distillate, the methanol concentration in the reaction distillation zone will be relatively quite low, about 1%. If the net methanol flow into the column is higher than the azeotrope, the methanol concentration will increase (60% has been measured) until methanol leaves with the TAME bottoms product. Neither case is desirable, because at low concentration the conversion of isoamylene to TAME is low, whereas at high concentrations the TAME purity is affected by the presence of the excess methanol.

It as an advantage of the present invention that the methanol-hydrocarbon azeotrope is maintained throughout essentially all of the reaction distillation zone, maximizing conversion of the reactive olefins.

It is a second advantage of the present invention that the control of the methanol concentration in the liquid leaving the reaction distillation zone insures a methanol free ether product.

Finally, it is another advantage that a truncated methanol concentration profile improves controllability of the column.

SUMMARY OF THE INVENTION

The present invention is a method for controlling etherification reactions in catalytic distillation column reactor comprising maintaining the concentration of the alcohol just above the level wherein no azeotrope is formed in the overhead and just below the level wherein a full azeotrope is formed in the overhead when measured at the lower end of the catalytic distillation zone or below the catalytic distillation zone in the column. Preferably the control is maintained at the "mid-reflux" point in the column, which is understood to mean herein the liquid at the bottom of the catalytic distillation zone.

Surprisingly it was discovered that when running a reaction distillation column for the production of TAME from the reaction of isoamylenes and methanol the methanol concentration within the reaction distillation zone is very strongly dependent on the operating conditions. It is highly desirable to maintain active, dynamic control of the methanol with the column on a continuous basis. To this end an on line analyzer is provided which continuously measures and controls the methanol concentration at a point within the column by adjusting the methanol feed to the unit.

In one embodiment the total methanol feed to the fixed bed reactors is adjusted in response to the measured methanol concentration in the column. In a second embodiment the methanol feed is split into two streams, one going to the fixed bed reactor and the other to the column, either directly or mixed into the feed stream from the primary reactor. In a preferred embodiment the analyzer is of the infrared or near infrared variety because of its rapid response to changes in concentration.

DETAILED DESCRIPTION OF THE PREFERRED EMBODIMENTS

Figure 1:
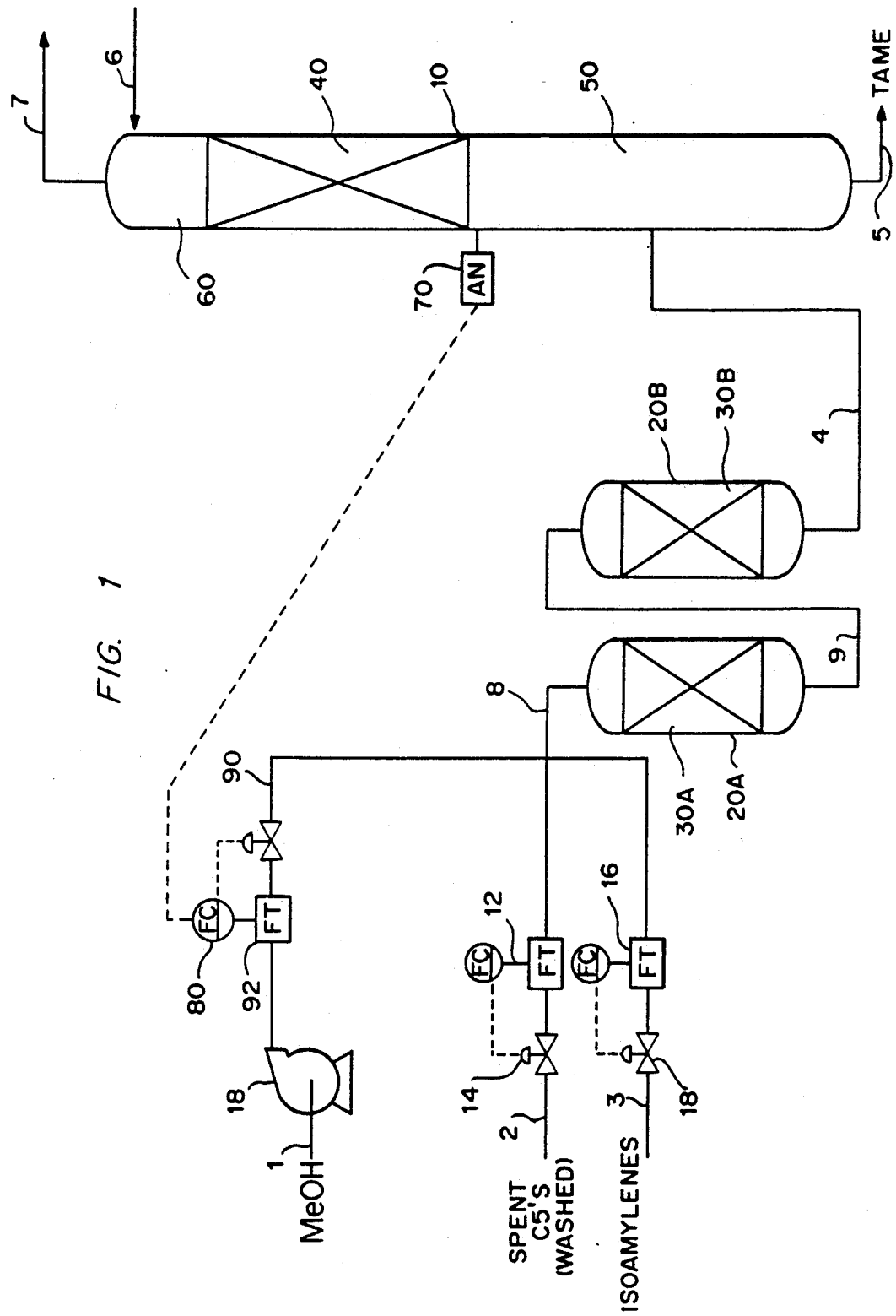
FIG. 1 is a simplified flow diagram of one embodiment of a process utilizing the invention.

U.S. Pat. Nos. 5,003,124 and 4,950,803 disclose a liquid i phase process for the etherification of $C_4$ and $C_5$ isoolefins with $C_1$ to $C_6$ alcohols in a boiling point fixed bed reactor that is controlled at a pressure to maintain the reaction mixture at its boiling point which may be directly attached to a catalytic distillation reactor.

The catalytic distillation process employs a catalyst system (See U.S. Pat. Nos. 4,215,011 and 4,302,356) which provides for both reaction and distillation concurrently in the same reactor, at least in part within the catalyst system. The method involved is briefly described as one where concurrent reaction and distillation occur in combination reactor-distillation structures which are described in several U.S. Pat. Nos. namely U.S. Pat. Nos. 4,242,530; 4,250,052; 4,232,177; 4,302,356; 4,307,254; and 4,336,407. Additionally U.S. Pat. Nos. 4,302,356 and 4,443,559 disclose catalyst structures which are useful as distillation structures.

For example, in this system and procedure, methanol and isoamylene (or the stream from the boiling point reactor which contains, ether, some unreacted isoolefin and methanol or make up methanol) containing $C_5$ stream are continuously fed to the reactor/distillation column where they are contacted in the catalytic distillation structure. The methanol preferentially reacts with isoamylene, forming TAME which is heavier than the $C_5$ components of the feed and the methanol, hence it drops in the column to form the bottoms. Concurrently, the unreacted $C_5$'s (e.g. n-pentane, n-pentenes) are lighter and form an overhead.

Catalysts preferred for the etherification process are cation exchangers, which contain sulfonic acid groups, and which have been obtained by polymerization or copolymerization of aromatic vinyl compounds followed by sulfonation.

The resulting products preferably contain an average of 1.3 to 1.8 sulfonic acid groups per aromatic nucleus. Particularly, suitable polymers which contain sulfonic acid groups are copolymers of aromatic monovinyl compounds with aromatic polyvinyl compounds, particularly, divinyl compounds, in which the polyvinyl benzene content is preferably 1 to 20% by weight of the copolymer (see, for example, German Patent specification 908,247).

The ion exchange resin is preferably used in a granular size of about 0.25 to 1 mm, although particles form 0.15 mm up to about 1 mm may be employed.

The resin catalyst is loaded into the fixed bed reactor as a fixed bed of the granules. The feed to the reaction is fed to the bed in liquid phase. The bed may be horizontal, vertical or angled. Preferably the bed is vertical with the feed passing downward through the bed and exiting, after reaction, through the lower end of the reactor.

A preferred catalytic distillation structure for use herein comprises placing the cation exchange resin particles into a plurality of pockets in a cloth belt, which is supported in the distillation column reactor by open mesh knitted stainless steel wire by twisting the two together in a helical form. This allows the requisite flows and prevents loss of catalyst. The cloth may be any material which is inert in the reaction. Cotton or linen are useful, but fiber glass cloth or "Teflon" cloth are preferred. The catalytic distillation structure when loaded into the column constitutes a distillation reaction zone.

Directly below the distillation reaction zone is a distillation zone containing inert distillation structure to effect the separation of unreacted methanol from the TAME product. A Model PA Infra Red Analyzer (IRA) obtained from ABB Process Analytics, Inc. is installed to sample and analyze the methanol concentration of the liquid leaving the distillation reaction zone (in catalytic distillation terminology the mid-reflux). The IRA can be connected to either the primary methanol flow control loop, injecting ahead of the fixed bed reactor, or to a secondary methanol control loop which injects to the fixed bed reactor effluent to the distillation column reactor directly. Both systems have been successfully tested, but the secondary methanol control provides faster and more responsive control.

On a commercial scale the sample point should be connected close to the "mid-reflux stream" or the "froth valve" if operating in the mode described in U.S. Pat. Nos. 4,978,807 and 5,120,404 which are hereby incorporated by reference. For the secondary methanol control scheme, a small stream of methanol, 5–10% of the total methanol requirement will bypass the fixed bed reactor (primary reactor). The flow of this methanol will be set by a flow controller and reset by the IRA controller. If the secondary methanol flow approaches its maximum or minimum the flow of the primary methanol will be adjusted to compensate. For optimal performance of the reaction distillation column the methanol concentration in the mid-reflux stream should be between 4–8 percent where the feed was $C_5$ stream and slightly lower when the feed is a $C_4$ or mixed $C_4/C_5$ feed.

Referring now to FIG. 1 there is shown a simplified flow diagram of a TAME process utilizing primary methanol control. Methanol is fed by pump 18 through flow line 1. The $C_5$'s are fed via flow lines 2 and 3 respectively and combined with the methanol in flow line 8 as feed to two fixed bed reactors 20A and 20B containing the cation exchange resin packing 30A and 30B as described above. The effluent from the last fixed bed reactor 30B is fed to a distillation column reactor 10 having a distillation reaction zone 40 in the upper portion. The unreacted isoamylenes remaining in the effluent react in the distillation reaction zone 40 with methanol to form tertiary amyl methyl ether (TAME) which is removed as bottoms via flow line 5. Distillation zone 50 is provided below the distillation reaction zone to separate the unreacted methanol from the TAME. If desired the liquid flowing down the column may be restricted to provide a froth within the distillation reaction zone as described in U.S. Pat. No. 4,978,807. Unreacted methanol and lighter inerts are removed as overheads via flow line 7. Preferably a portion of the overheads is condensed and returned as reflux via flow line 6.

A Model PA Infra Red Analyzer 70 provided by ABB Process Analytics, Inc. is installed to sample and analyze the methanol concentration of the liquid (mid-reflux) a it leaves the reaction distillation zone 40. The IRA is operably connected to flow control loop 80 which controls flow control valve 90. The methanol feed rate is controlled such that the concentration in the mid-reflux is between 4–8%.

Figure 2:
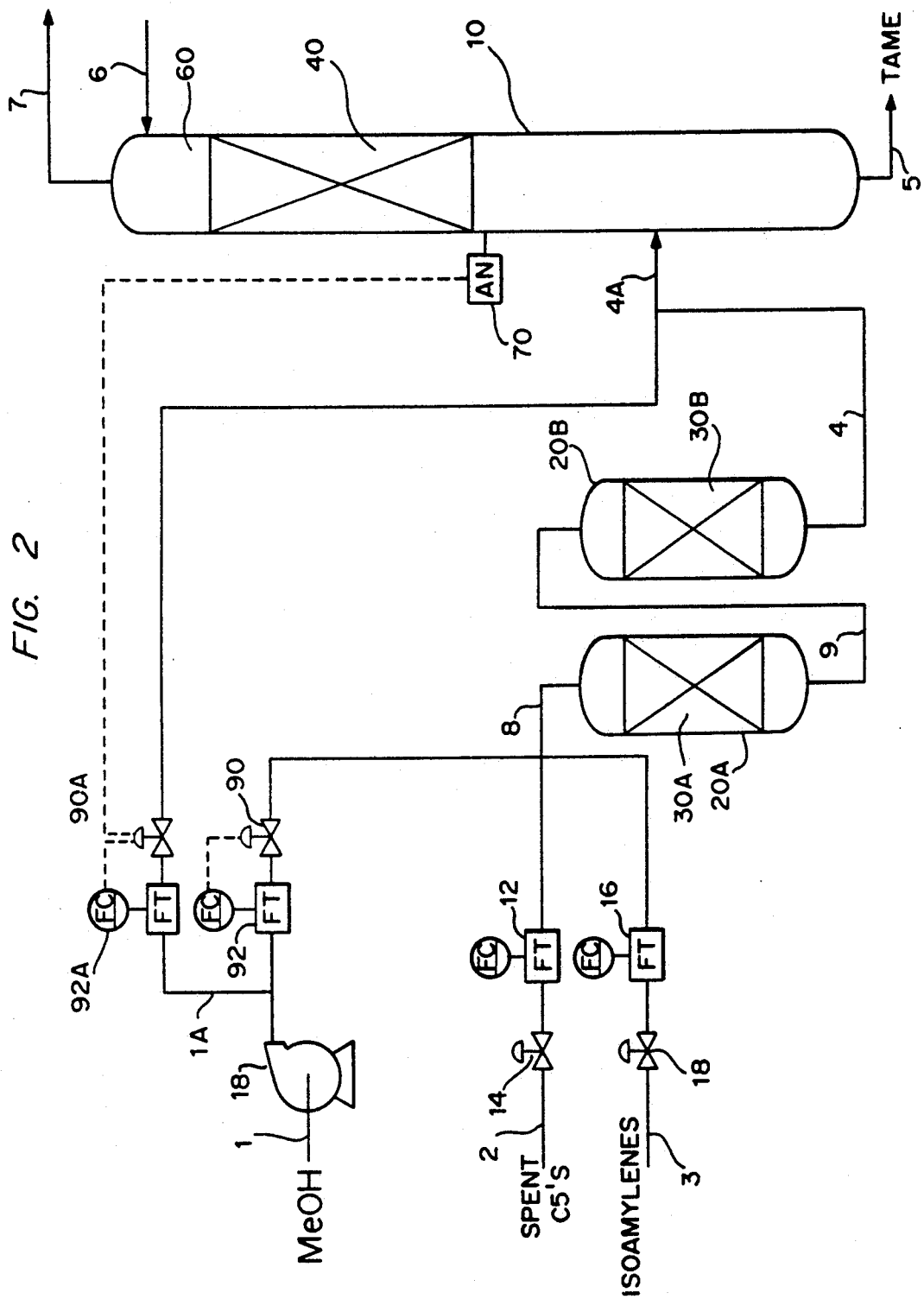
FIG. 2 is a simplified flow diagram of a second embodiment of a process utilizing the invention.

Referring now to FIG. 2 a simplified flow diagram of the secondary methanol control scheme is shown. The equipment and flow are essentially the same as in FIG. 1 except a slip stream 1A of methanol is removed from flow line 1 before control loop 92. A second control loop 92A is located in flow line 1A which responds to the IRA 70 controlling the flow of methanol through flow line 1A directly to the distillation column reactor. If the flow through flow line 1A approaches either the minimum or maximum flow control loop 92 is reset to compensate by adding or reducing the primary methanol feed rate.

Figure 3:
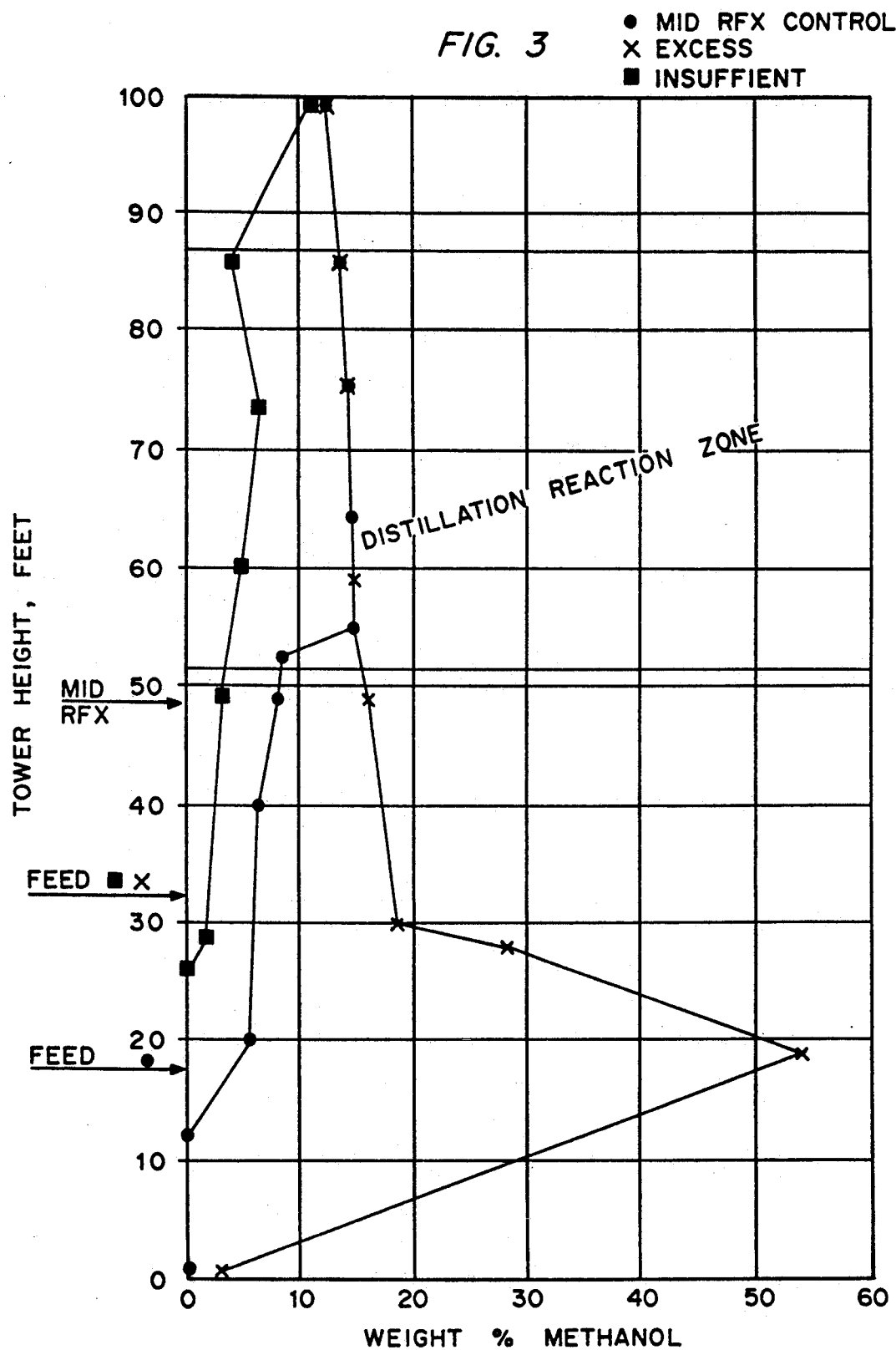
FIG. 3 is a graphical presentation of the methanol concentration profile within a distillation column reactor utilizing the invention.

Referring now to FIG. 3 there is shown a comparison of the methanol concentration profiles when there is insufficient methanol feed, excess methanol feed, and when the methanol feed is controlled by the mid-reflux concentration at about 8 per cent. As may be seen, when there is a shortage of methanol feed, there is only about 4–8 per cent excess methanol in the reaction distillation zone. It has been noted that such a profile reduces the conversion of the isoolefins by up to 30%.

While the methanol concentration profile in the reaction distillation zone is adequate when excess methanol is fed, there is about 3 per cent methanol in the bottoms TAME produce. When the methanol concentration in the mid-reflux (liquid leaving the distillation reaction zone) is controlled at about 8 per cent the same profile in the reaction distillation zone is achieved as with excess methanol feed. However, there is no methanol in the bottoms.

While the control scheme has been shown primarily for the production of TAME the same scheme could be used in the MTBE process. This would be especially useful wherein the $C_4$ feed stream includes a high concentration of the reactive $iC_4=$. The high concentration of the $iC_4=$ requires balancing a large methanol feed flow with the demands of the entire system. The analyzer and control system would be very advantageous in preventing excess or shortage of methanol.

Another process which is benefited by the use of the analyzer control scheme is a process which feeds a combined $C_4/C_5$ stream and produces TAME and MTBE.

The invention claimed is:

1. In a process for the production of ethers from the reaction of isoolefins with an alkyl alcohol in a distillation column reactor having a distillation reaction zone above a distillation zone, the improvement comprising determining the concentration of alcohol at the lower end of or a point below the distillation reaction zone and maintaining the concentration of the alcohol just above the level wherein no azeotrope is formed in the overhead and just below the level wherein a full azeotrope is formed in the overhead.

2. The process according to claim 1 wherein the alcohol comprises methanol and the concentration is controlled by measuring the concentration by an infrared analyzer.

3. The process according to claim 1 wherein said alcohol is methanol, said isoolefin is isoamylene, and said point is directly below said distillation reaction zone.

4. The process according to claim 3 wherein said methanol concentration in the liquid directly below said distillation reaction zone is controlled between 4 and 8 wt %.

5. A process for the production of tertiary amyl methyl ether comprising the steps of:
   (a) feeding a first stream containing $C_5$ hydrocarbons including isoamylenes to a fixed bed straight pass reactor containing an acid cation exchange resin catalyst;
   (b) providing a second stream containing methanol to said process;
   (c) feeding said second stream to said fixed bed reactor whereby a portion of said isoamylenes is reacted with a portion of said methanol to produce a third stream containing tertiary amyl methyl ether, unreacted methanol and unreacted isoamylenes;
   (d) feeding said third stream along with a fourth stream comprising methanol to a distillation column reactor containing a second fixed bed acid cation exchange resin in the form of a catalytic distillation structure wherein a substantial portion of said unreacted isoamylenes is reacted with methanol to form additional tertiary amyl methyl ether while concurrently separating by fractional distillation unreacted methanol from tertiary amyl methyl ether, said tertiary amyl methyl ether being removed from said distillation column reactor as bottoms and said unreacted methanol along with any unreacted $C_5$'s are removed overheads;
   (e) measuring the concentration of methanol in said distillation column reactor directly below said second fixed bed; and
   (f) controlling the concentration of methanol in said distillation column directly below said second fixed bed at just above the level wherein no azeotrope is formed in the overhead and just below the level wherein a full azeotrope is formed in the overhead.

6. The process according to claim 5 wherein said concentration of methanol in step (f) is controlled at 4–8%.

* * * * *